US011813235B2

(12) United States Patent
Seyedsayamdost et al.

(10) Patent No.: US 11,813,235 B2
(45) Date of Patent: Nov. 14, 2023

(54) GUANFACINE AS AN ANTI-VIRULENCE AGENT

(71) Applicant: The Trustees of Princeton University, Princeton, NJ (US)

(72) Inventors: Mohammad R. Seyedsayamdost, Princeton, NJ (US); Bethany K. Okada, San Diego, CA (US); Anran Li, Plainsboro, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 711 days.

(21) Appl. No.: 16/824,968

(22) Filed: Mar. 20, 2020

(65) Prior Publication Data
US 2020/0297669 A1  Sep. 24, 2020

Related U.S. Application Data

(60) Provisional application No. 62/822,519, filed on Mar. 22, 2019.

(51) Int. Cl.
*A61K 31/155* (2006.01)
*A61P 31/04* (2006.01)
*A61K 45/06* (2006.01)

(52) U.S. Cl.
CPC ............ *A61K 31/155* (2013.01); *A61P 31/04* (2018.01); *A61K 45/06* (2013.01)

(58) Field of Classification Search
None
See application file for complete search history.

(56) References Cited

U.S. PATENT DOCUMENTS 8,283,350 B2 * 10/2012 Horn .................... A61K 9/0043
514/567

OTHER PUBLICATIONS

Posey et al., Guanfacine and Guanfacine Extended Release: Treatment for ADHD and Related Disorders. CNS Drugs Reviews, 2007, 13, 465-474.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*

* cited by examiner

*Primary Examiner* — Po-Chih Chen
(74) *Attorney, Agent, or Firm* — MEAGHER EMANUEL LAKS GOLDBERG & LIAO, LLP

(57) ABSTRACT

Disclosed are methods for using guanfacine, an analog or derivative of guanfacine, or a pharmaceutically acceptable salt thereof, to reduce the virulence of a bacterial pathogen. When treating a patient, the method generally involves administering to the patient a therapeutically effective dose of guanfacine, an analog or derivative of guanfacine, or a pharmaceutically acceptable salt thereof. An alternative method involves contacting the bacterial pathogen with guanfacine, an analog or derivative of guanfacine, or a pharmaceutically acceptable salt thereof.

10 Claims, 6 Drawing Sheets

GUANFACINE AS AN ANTI-VIRULENCE AGENT

CROSS-REFERENCE TO RELATED APPLICATIONS

This application claims priority to U.S. Provisional Patent App. No. 62/822,519, filed Mar. 22, 2019, which is herein incorporated by reference in its entirety.

STATEMENT REGARDING FEDERALLY SPONSORED RESEARCH OR DEVELOPMENT

This invention was made with government support under Grant No. AI124786 awarded by the National Institutes of Health. The government has certain rights in the invention.

BACKGROUND

Antibiotics have saved countless lives and provided immense insights into bacterial physiology. Yet, the very nature of antibiosis creates selective pressures that lead to the emergence of resistant phenotypes, which in turn forge a cyclical need for new antibiotics. To break the antibiotics-resistance arms race, new strategies are needed in the fight against infectious disease. One such strategy involves inhibiting virulence without retarding bacterial growth, thereby eliminating conditions that favor resistance.

Several approaches have been employed for identifying anti-virulence agents in bacterial pathogens, notably *Staphylococcus aureus* and *Pseudomonas aeruginosa*. These studies have typically targeted master regulators of virulence (such as two-component systems or quorum sensing), recalcitrance to host defenses or antibiotics (e.g. biofilm formation), or specific virulence factors (such as secretion systems or proteases). However, no candidate compound has been identified that suppresses the biosynthesis of multiple virulence factors.

BRIEF SUMMARY

The present disclosure is drawn to the use of guanfacine, an analog or derivative of guanfacine, or a pharmaceutically acceptable salt thereof, to reduce the virulence of a bacterial pathogen, via, e.g., administering to a patient infected with the bacterial pathogen, applying to a surface containing the bacterial pathogen, etc.

A first aspect of the present disclosure is drawn to a method for treating a patient with an infection from a bacterial pathogen, such as *Pseudomonas aeruginosa*, involving the administration to the patient a therapeutically effective dose of guanfacine, an analog or derivative of guanfacine, or a pharmaceutically acceptable salt thereof. Preferably, this method also involves administering to the patient at least one additional means of treatment, such as administration of one or more antibacterial agents. Optionally, the therapeutically effective dose is a dose having a concentration of guanfacine, analog or derivative of guanfacine, or pharmaceutically acceptable salt thereof of less than 100 µM.

A second aspect of the present disclosure is drawn to a method for inhibiting production of at least one virulence factor in a bacterial pathogen, such as *Pseudomonas aeruginosa*, involving contacting the bacterial pathogen with guanfacine, an analog or derivative of guanfacine, or a pharmaceutically acceptable salt thereof. Preferably, this method also involves administering at least one additional means for treating the bacterial pathogen, such as administration of one or more antibacterial agents.

Optionally, the virulence factors that are inhibited are a phenazine, an alkaline protease, the Pseudomonas quinolone signal (PQS), hydrogen cyanide, phospholipase C, pyocyanin, alginate, a biofilm, or a combination thereof. Optionally, two or more virulence factors are down-regulated. Optionally, at least seven virulence factors are inhibited.

Optionally, the guanfacine, analog or derivative of guanfacine, or pharmaceutically acceptable salt thereof targets at least a QseC homolog in the bacterial pathogen.

DETAILED DESCRIPTION

The present disclosure is drawn to a method for reducing the virulence of a bacterial pathogen, e.g., within a patient, on a surface, etc. Thus, one method is drawn to treating a patient with an infection from a bacterial pathogen, while a second method is drawn to inhibiting production of at least one virulence factor in a bacterial pathogen.

In preferred embodiments, the bacterial pathogen is one of the ESKAPE pathogens—*Enterococcus faecium, Staphylococcus aureus, Klebsiella pneumoniae, Acinetobacter bau-* mannii, *Pseudomonas aeruginosa*, and/or *Enterobacter* spp. In more preferred embodiments, the bacterial pathogen is *Pseudomonas aeruginosa*.

The disclosed methods involve either (a) the administration to the patient a therapeutically effective dose of guanfacine, an analog or derivative of guanfacine, or a pharmaceutically acceptable salt thereof, or (b) contacting the bacterial pathogen with guanfacine, an analog or derivative of guanfacine, or a pharmaceutically acceptable salt thereof.

In certain embodiments, the analog or derivative of guanfacine has the structure $R^1$—$R^2$—CONH—$R^3$, where $R^1$ is an optionally substituted phenyl or benzyl group, preferably substituted with at least one halogen, $R^2$ is a methylene unit or a C1-C6 alkyl group that is saturated or unsaturated, and $R^3$ is a carboxamidine.

In certain embodiments, the therapeutically effective dose is a dose having a concentration of guanfacine, analog or derivative of guanfacine, or pharmaceutically acceptable salt thereof of less than 1000 μM, preferably less than 500 μM, more preferably less than 250 μM, and still more preferably less than 100 μM.

In certain embodiments, the virulence factors that are inhibited are a phenazine, an alkaline protease, the Pseudomonas quinolone signal (PQS), hydrogen cyanide, phospholipase C, pyocyanin, alginate, a biofilm, or a combination thereof. In certain embodiments, two or more virulence factors are down-regulated. In certain embodiments, at least seven virulence factors are inhibited.

In certain embodiments, a patient's treatment is administered in any known, appropriate method, which may include (i) physical application of, e.g., a cream, gel, or spray; (ii) orally; (iii) via inhalation; (iv) via a transdermal patch, or (v) via a subdermal injection.

In certain embodiments, a surface may be treated by, e.g., spraying or wiping a surface that is possibly or actually infected with the bacterial pathogen, where the spray or wipe comprises a carrier fluid containing the guanfacine, an analog or derivative of guanfacine, or a pharmaceutically acceptable salt thereof. In other embodiments, an instrument believed to be infected may be submerged in a solution comprising the guanfacine, an analog or derivative of guanfacine, or a pharmaceutically acceptable salt thereof.

Figure 1:
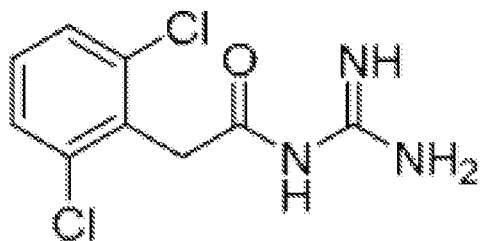
FIG. 1 shows the structure of guanfacine.
Figure 2:
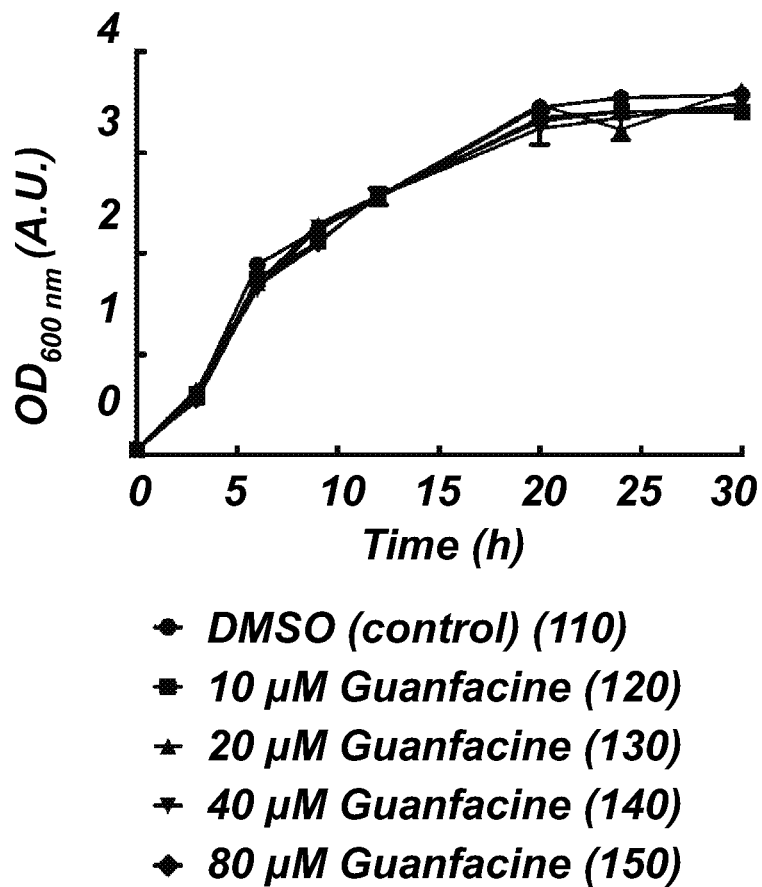
FIG. 2 is a graph showing the growth curve of *P. aeruginosa* in the absence (DMSO) and presence of guanfacine in various concentrations (10 µM, 20 µM, 40 µM, and 80 µM).

Guanfacine is not growth-inhibitory as shown by the growth curves of untreated and guanfacine-treated cultures. As seen in FIG. 2, the DMSO-only control (110) had a statistically similar growth curve to those cultures treated with 10 μM (120), 20 μM (130), 40 μM (140), and 80 μM (150) of Guanfacine.

Figure 3A:
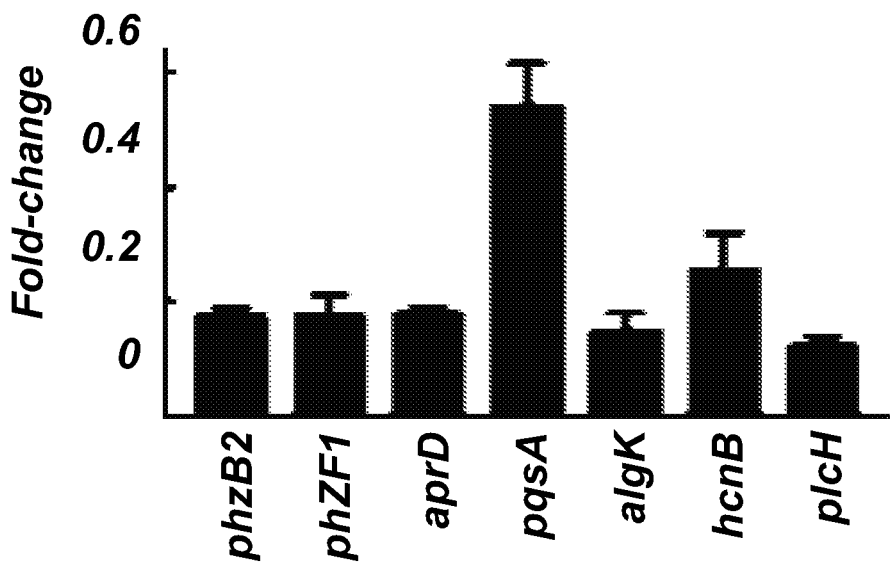
FIG. 3A is a graph showing the transcriptional down-regulation of seven virulence genes by guanfacine relative to an untreated control.

The effect of guanfacine on the expression of virulence factors was verified in flask cultures. As seen in FIG. 3A, a 2-9-fold reduction across seven reporter strains was observed.

Figure 3B:
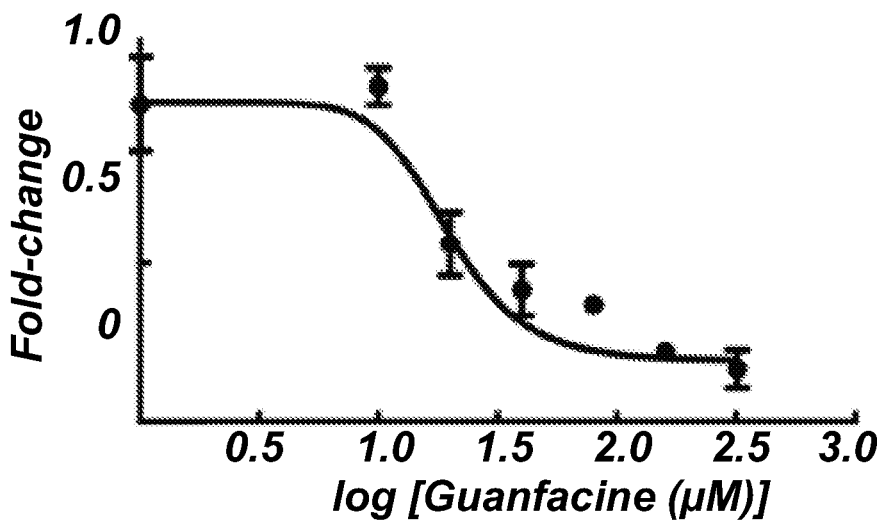
FIG. 3B is a graph showing the dose-response of phzB2-lacZ as a function of guanfacine concentration.

The expression of phzB2, involved in phenazine biosynthesis, appeared to be among the most down-regulated. As seen in FIG. 3B, a dose-response curve with the phzB2 reporter gave an IC50, the concentration of guanfacine at which half-maximal down-regulation was observed, of 19 μM.

Figure 3C:
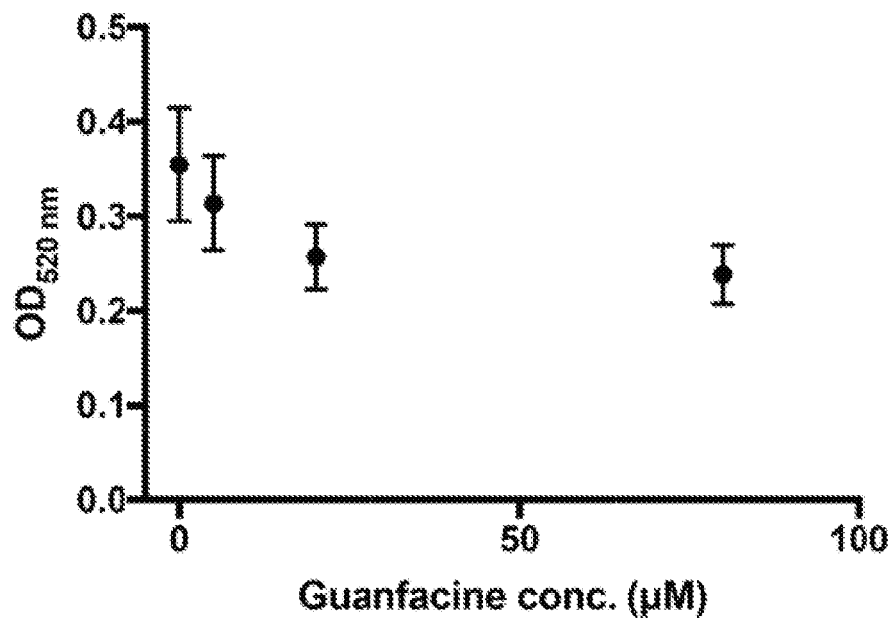
FIG. 3C is a graph showing the dose-dependent reduction of pyocynanin biosynthesis as a function of guanfacine concentration.
Figure 3D:
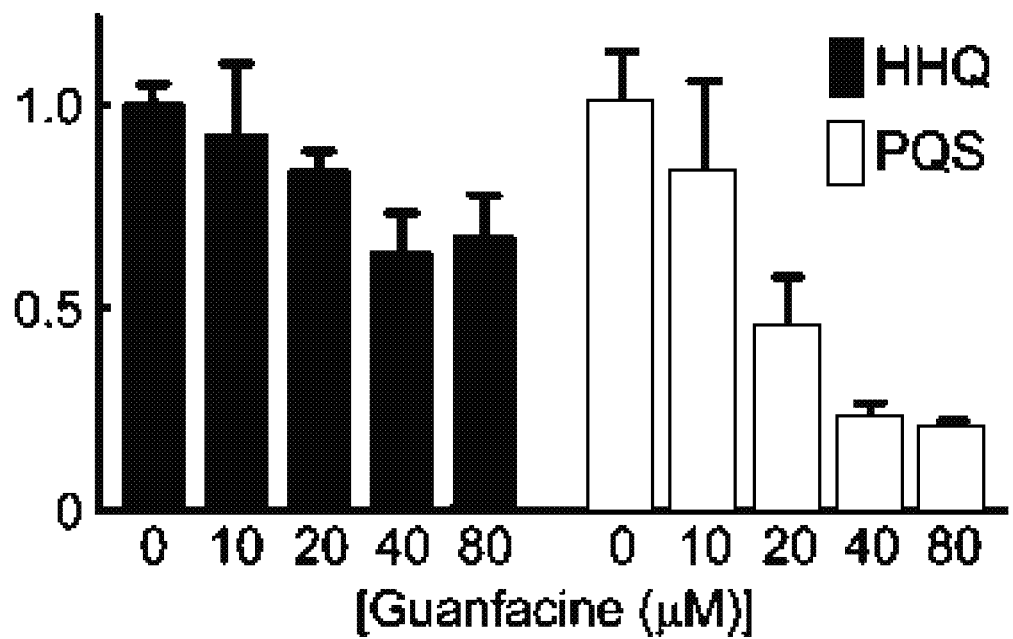
FIG. 3D is a graph showing the relative quantification of HHQ and PQS produced by wt *P. aeruginosa* as a function of guanfacine concentration, normalized to an untreated control.
Figure 3E:
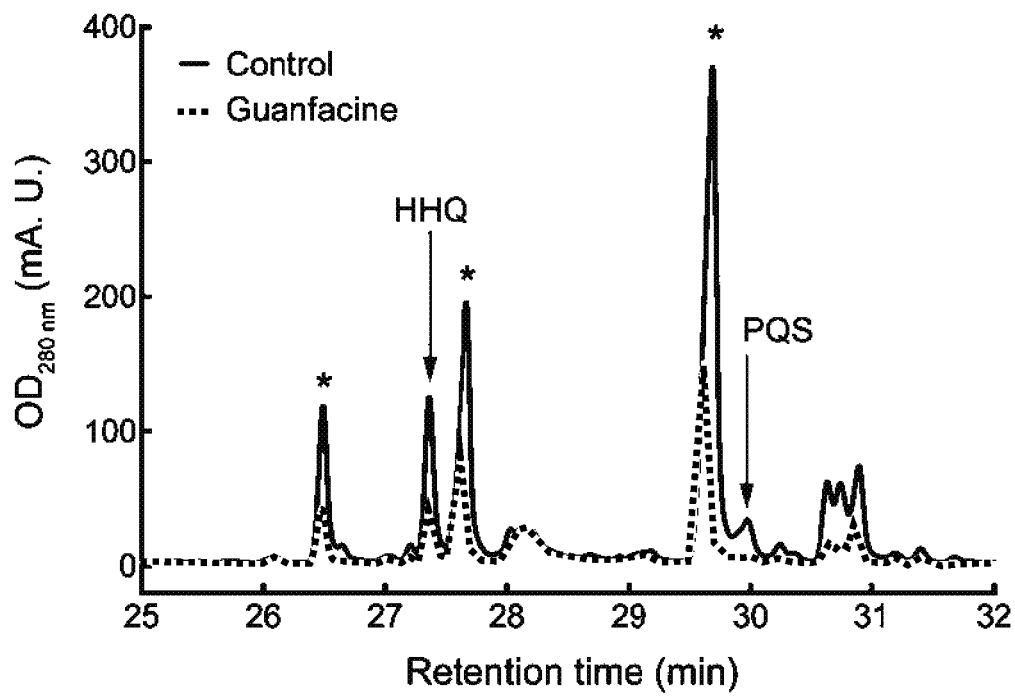
FIG. 3E is a graph of an HPLC analysis of cell-free supernatants of *P. aeruginosa* in the absence (solid lines) or presence (dashed lines) of 40 µM guanfacine, showing the effect of guanfacine on quinolone production in *P. aeruginosa*. This HPLC analysis of cell-free supernatants of *P. aeruginosa* in the absence (solid lines) or presence (dashed lines) of 40 µM guanfacine. Peaks corresponding to HHQ and PQS are labeled, peaks of other quinolones are indicated with an asterisk.
Figure 4:
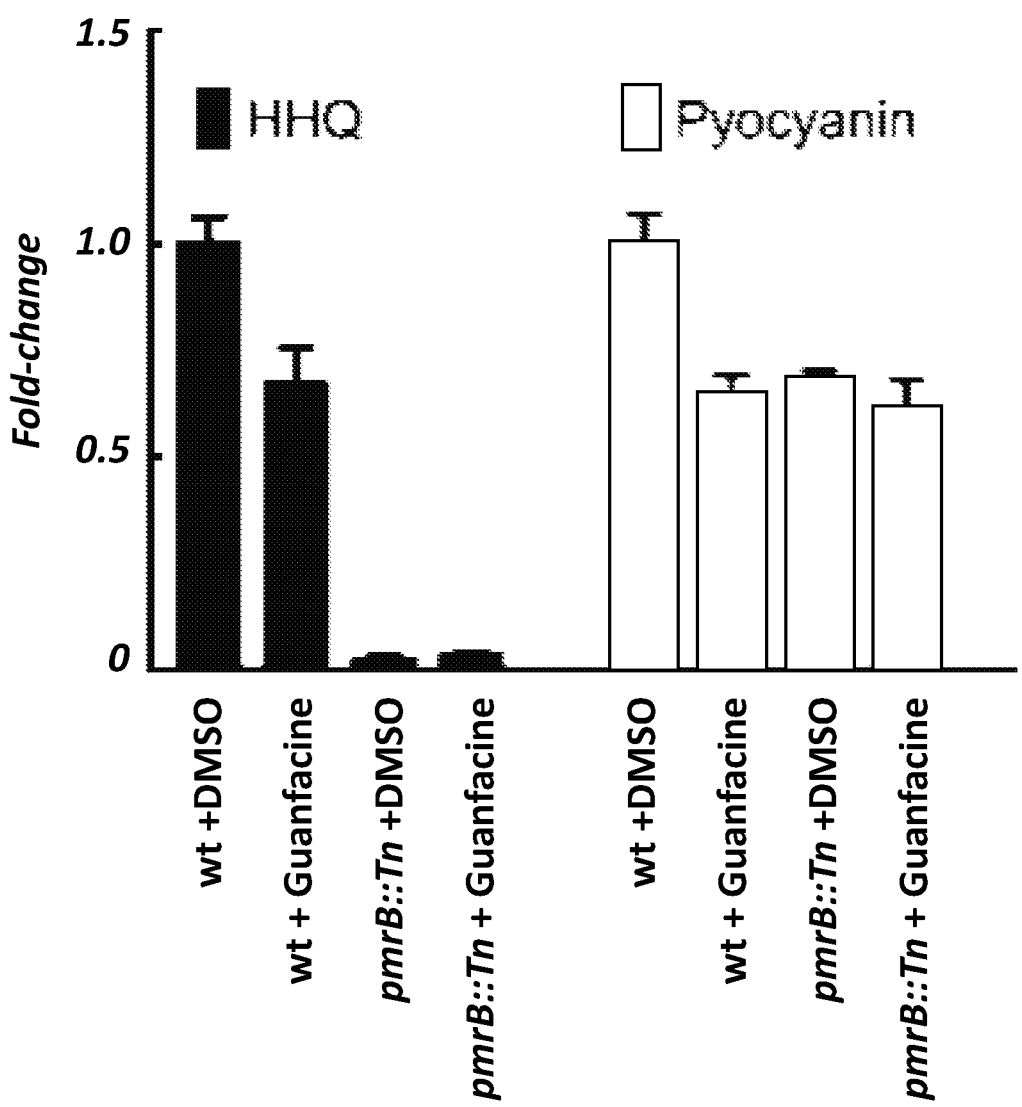
FIG. 4 is a graph of the quantification of the levels of HHQ (black bars) and pyocyanin (white bars) in guanfacine-treated and untreated cultures.

The effects of guanfacine were probed further by measuring the levels of pyocyanin, a downstream product of phenazine. Pyocyanin is the blue secondary metabolite responsible for both the toxicity and characteristic color of *P. aeruginosa*. Extraction of untreated and guanfacine-treated cultures revealed a 1.5-fold reduction in the levels of pyocyanin, in a guanfacine concentration-dependent manner (See FIG. 3C). Without being bound to a particular theory, the likely cause of the incomplete suppression of pyocyanin synthesis is the existence of two independently-expressed copies of the phenazine biosynthetic operon. Nonetheless, the direct measurement of pyocyanin corroborates results observed with the reporter strains. The production of both phenazines and pyocyanin is known to be regulated by the las and pqs QS circuits. Specifically, in response to 3O-C12-HSL, LasR induces expression of the pqs operon and the LysR-type regulator, PqsR. The PQS/PqsR complex then activates phenazine and pyocyanin synthesis. To verify that guanfacine acts upstream of both products, levels of quinolines were directly measured. Guanfacine treatment led to decreased levels of both HHQ and PQS as well as several other quinolines, as determined by HPLC-MS. See FIGS. 3D, 3E. Notably, as seen in FIG. 3D, 4.5-fold less PQS was observed in the presence of 40 μM guanfacine, relative to DMSO-treated control cultures.

Figure 3F:
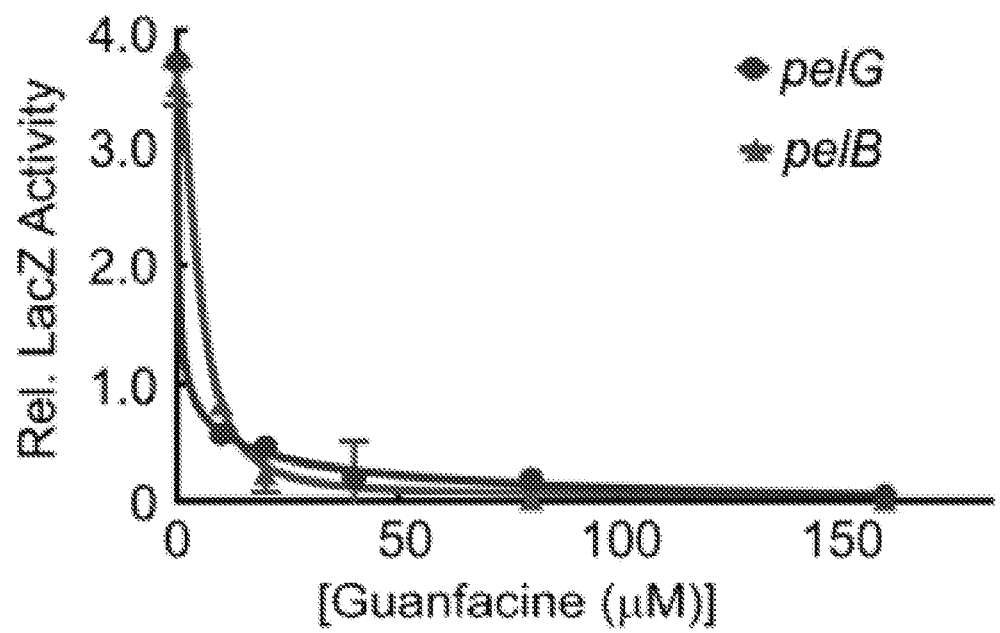
FIG. 3F is a graph of the dose-response of the expression of pelG and pelB, involved in biofilm production, as a function of guanfacine concentration, using the appropriate LacZ reporter strain.

Another important virulence determinant in *P. aeruginosa* is biofilm formation. A cluster of genes, termed pel regulated by the las QS system, have been established as responsible for producing the biofilm matrix exopolysaccharide. Two reporter strains carrying translational lacZ fusions (pelB-lacZ and pelG-lacZ) were subjected to guanfacine dose-response analysis. As seen in FIG. 3F, an IC50 of 5.8 μM (pelB) and 3.1 μM (pelG) was obtained for these strains, consistent with the down-regulatory role of guanfacineon other QS-regulated behaviors. Nearly complete suppression of pelB and pelG expression was observed at 80 μM guanfacine.

Together, the data above demonstrate that guanfacine is a pleiotropic anti-virulence agent in *P. aeruginosa* down-regulating proteins involved in biofilm formation and the synthesis of both proteinaceous and small molecule virulence factors.

Having established guanfacine's effect on *P. aeruginosa*, its potential target was also addressed. QseC is a membrane-embedded sensor His kinase that forms a two-component regulatory circuit with QseB. Diverse pathogens use QseC to sense host-derived adrenergic signals and bacterially-produced autoinducer-3 (AI-3), upon which a phospho-relay ensues leading to the phosphorylation of the response regulator QseB, which initiates transcription of key virulence genes. It was posited that guanfacine could also act through the same target in *P. aeruginosa*, in which the QseC and QseB homologs have been termed PmrA and PmrB, respectively.

To explore this idea, a mutant carrying a transposon insertion in pmrB (pmrB::Tn) was tested. Both wt and mutant strains were grown in the presence of guanfacine or DMSO (control), and the production of HHQ was quantified directly using HPLC-MS, while pyocyanin synthesis was assessed as previously reported. The results showed that the mutant pmrB::Tn strain produced lower levels of both virulence factors than the wt strain, consistent with a role for this two-component system in virulence factor production (FIG. 4). The mutation had a pronounced effect on HHQ production, lowering it 35-fold, whereas the production of pyocyanin levels were reduced 1.5-fold. Importantly, no further effect was observed when pmrB::Tn cultures were supplemented with guanfacine (FIG. 4). In the absence of the sensor His kinase, guanfacine was unable to exert its down-regulatory effect, especially with pyocyanin where significant production remained. These results are consistent with guanfacine acting through the QseC homolog in *P. aeruginosa*, though at this point, other targets cannot be excluded.

Thus, in some embodiments, the guanfacine, analog or derivative of guanfacine, or pharmaceutically acceptable salt thereof targets at least a QseC homolog in the bacterial pathogen.

Preferably, this method also involves administering to the patient at least one additional means of treating the bacterial pathogen. The additional means can be any additional means known to those of skill in the art, and may include, e.g., administering one or more antibacterial agents, including bactericidal or bacteriostatic antibiotics or proteins. In some embodiments, the antibacterial agent is a penicillin, cephalosporin, or any beta-lactam antibiotic, a fluoroquinolone, or an aminoglycoside.

In one example, reporter genes for the various virulence factors encoded in the *P. aeruginosa* genome were selected. Seven reporter strains from the sequence-verified transposon mutant library generated by Manoil and colleagues were identified, in which transposons carrying a promoterless lacZ reporter were inserted into the genome of *P. aeruginosa*. The strains selected carried an in-frame lacZ reporter in aprD (alkaline protease), pqsA (PQS biosynthesis), hcnB (HCN biosynthesis), algK (alginate biosynthesis), phzB2 and phzF1 (phenazine biosynthesis from two different gene clusters), and plcH (phospholipase C). Growth and high-throughput LacZ assays were optimized in a 384-well plate format using three reporter strains In order to identify down-regulators of virulence, rather than growth-inhibitors of *P. aeruginosa*, special care was taken to eliminate compounds that (i) interfered with the LacZ assay and (ii) affected *P. aeruginosa* growth. By carrying out an ex vivo LacZ assay, all LacZ assay inhibitors in a library of small molecules were identified. Growth-inhibition assays using the small molecule library were performed by monitoring optical density at 600 nm ($OD_{600\ nm}$). Some compounds retarded the growth of each reporter strain by more than 50% (relative to the untreated strain) These are shown along with the percent growth inhibition in Table 1, below. For the purposes of screening for virulence, these compounds were excluded, although such compounds can be used as an additional treatment option.

TABLE 1

Percent growth inhibition of *P. aeruginosa* in the presence of the compound indicated.

| Compound | % Growth Inhibition |
| --- | --- |
| Colistin, Chlorhexidine | 96 |
| Silver sulfadiazine, Mitomycin C, Levofloxacin, Hexachlorophene, Auranofin | 93-94 |
| Rifamixin, Rifampin, Rifapentine, Rifabutin, Minocycline, Moxifloxacin, Ciprofloxacin | 85-88 |
| Mechlorethamine | 84 |
| Gemifloxacin, Ofloxacin, Norfloxacin, Gatifloxacin | 79-83 |
| Fingolimod | 76 |
| Trimethoprim, Estradiol | 73 |
| Doripenem, Mitotane | 69-71 |
| Chloramphenicol | 64 |
| Tamoxifen | 57 |
| Micafungin | 54 |

The list contains in general well-known antibiotics. Perhaps most surprising among these is the observation that the estrogen hormone, estradiol, and the multiple sclerosis drug fingolimod exhibit strong growth-inhibitory activity toward *P. aeruginosa*.

With high-throughput growth and LacZ assays established, each reporter strain was screened in biological duplicates against a library of 770 FDA-approved drugs, with the goal of potentially repurposing compounds that have already passed FDA safety criteria. Each experiment contained a negative control, the test strain in the absence of compounds from the small molecule library, as well as a positive control, the phzB2-lacZ reporter, which monitors phenazine production and gave the strongest signal during method development. After a defined growth period, the expression of each of the seven reporter strains was determined using high-throughput LacZ assays. The LacZ activity was normalized relative to the negative control. The $log_{10}$ of the fold-change for each of the seven strains were combined and colorized to produce an anti-virulence heat-map. Most compounds within this set of FDA-approved drugs did not exhibit significant effects. Nonetheless, the heat-map brought four groups of compounds into focus that seemed to modulate virulence gene expression: Anti-inflammatory drugs that target prostaglandin synthase included several compounds, such as ibuprofen, ketoprofen, and naproxen, that down-regulated virulence factor expression. A similar effect was observed for the anti-hypertensive drug, guanfacine, and for three anti-Parkinson's drugs, tolcapone, entacapone, and apomorphine . By contrast, several beta-lactams, such as piperacillin and cephalosporin antibiotics appeared to further enhance the expression of virulence factors. Because of the previously-established roles of anti-inflammatory agents as potential quorum quenchers in *P. aeruginosa*, the effects of cephalosporins and guanfacine were focused on in further detail.

The effect of cephalosporins was especially surprising as some, such as cefepime or ceftazidime, are used clinically to fight *P. aeruginosa* infections. While at high concentrations, they inhibit *P. aeruginosa* growth, at low doses, they appear to enhance virulence gene expression. A similar phenomenon is observed with *B. thailandensis*, where the otherwise silent virulence factor malleilactone (or burkholderic acid) is only produced in laboratory cultures upon treatment with the antibiotic trimethoprim. Interestingly, later-generation cephalosporins (see Table 2, below) that are more effective antibiotics also appeared to be more effective inducers of virulence, implying that growth inhibition and virulence factor production are linked.

TABLE 2

A cephalosporin representative of each generation.

| Generation | Representative Structure |
| --- | --- |
| $1^{st}$ | 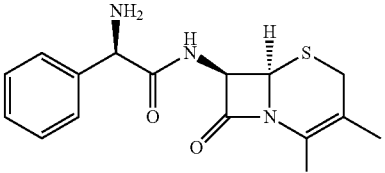 (6) |
| $2^{nd}$ | 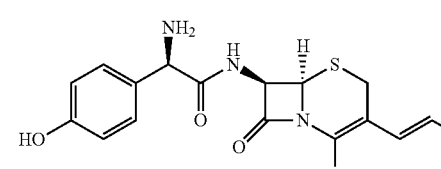 (7) |

TABLE 2-continued

A cephalosporin representative of each generation.

| Generation | Representative Structure |
|---|---|
| 3rd | 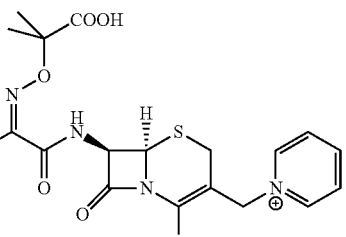 (8) |
| 4th | 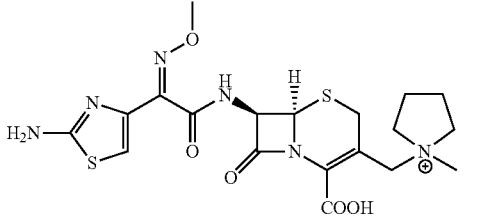 (9) |

Figure 5A:
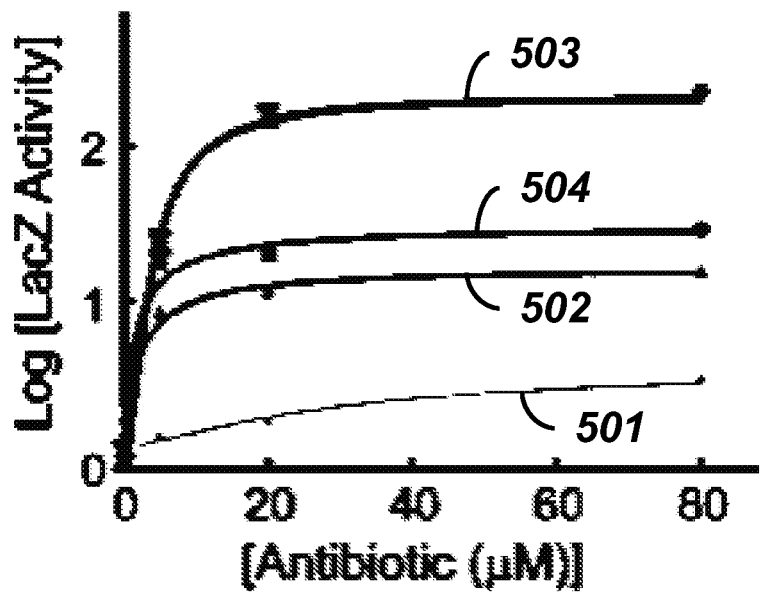
FIG. 5A is a graph illustrating dose-dependent induction of phzF1-lacZ as a function of antibiotic concentration. The $OD_{600\ nm}$-normalized LacZ activity is shown.
Figure 5B:
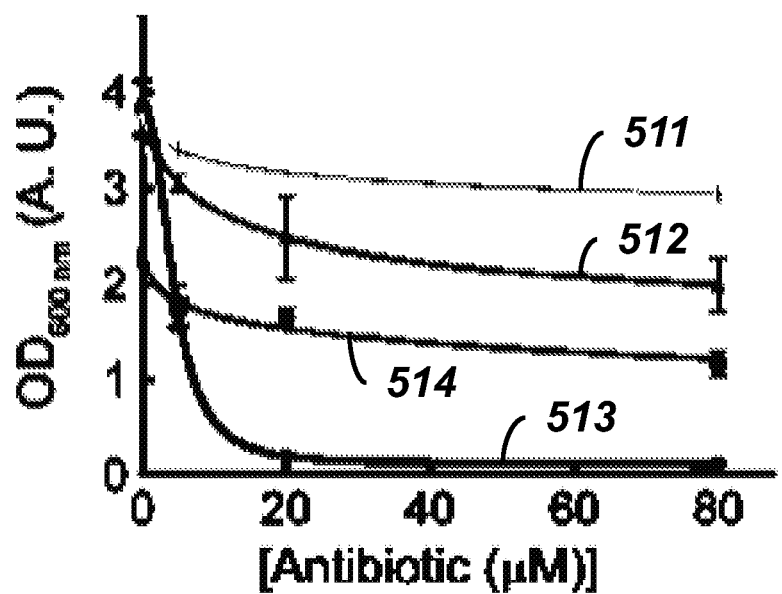
FIG. 5B is a graph illustrating dose-dependent growth inhibition of phzF1-lacZ as a function of antibiotic concentration.

Low and high doses of selected cephalosporins and beta-lactams were further evaluated, and the effects of cefprozil (7), ceftazidime (8), cefepime (9), and piperacillin on *P. aeruginosa* growth and virulence was investigated. Consistent with the screening results, a 3 to 200-fold induction of phzF1 at optimal concentrations of each antibiotic was observed. See FIG. 5A (cefprozil (501), ceftazidime (502), cefepime (503) and piperacillin (504)). The trend of the later-generation cephalosporins killing more effectively at high doses and, at the same time, inducing virulence more effectively at low doses, held up. Specifically, cefprozil (7), ceftazidime (8), and cefepime (9) exhibited growth-inhibitory IC50 values of 362 µM, 53 µM, and 4.6 µM, respectively (See FIG. 5A). At the same time, they exhibited EC50 values (the concentration at which induction of phzF1-lacZ was half-maximal) of 58 µM (7), 21 µM (8), and 14 µM (9). See FIG. 5B (cefprozil (511), ceftazidime (512), cefepime (513) and piperacillin (514)). Piperacillin, a 4th-generation penicillin gave IC50 and EC50 values of 6.4 µM and 8.4 µM, respectively.

In some embodiments, the additional treatment may involve the application of an antiseptic or disinfectant.

In some embodiments, the additional treatments are co-administered.

In various examples, bacterial growth was carried out in LB supplemented with 50 mM Mops, pH 7.0 (hereafter, LB-Mops). To commence a screen, a *P. aeruginosa* reporter strain from an LB agar plate was used to inoculate 5 mL of LB-Mops medium in a sterile 14-mL bacterial culture tube. The culture was grown for 4 h at 30° C./250 rpm. After 4 h, its optical density ($OD_{600\ nm}$) was determined on a Cary 60 UV-visible spectrophotometer (Agilent). The culture was diluted into 100 mL of LB-Mops to give a final $OD_{600\ nm}$ of 0.05. Subsequently a volume of 50 µL was dispensed into each of six sterile, 384 well plates (Corning) using a Multiflo Microplate Dispenser (Biotek). Candidate elicitors were added to the plates using a CyBi-Well automated liquid transfer robot (CyBio). Each well was supplemented with 0.2 µL of a compound from the Enzo Scientific FDA approved drug library, which comprises 770 molecules. The compounds were dispensed into columns 3 through 22 on each plate. Columns 2 and 23 contained the negative control (the reporter strain being tested in the absence of any compounds), and columns 1 and 24 contained the positive control (e.g., strain phzB2-lacZ). Each compound was tested in duplicate, using three 384-well plates per set. Each plate was covered with a Breathe-Easy sealing membrane (Sigma) and cultured at 30° C./250 rpm in a Multitron Shaker (ATR) equipped with green sealing tray. To maintain constant humidity, several 1-L Erlenmeyer flasks containing 200 mL of sterile water were also placed inside the shaker. After 12 h, the plates were removed from the shaker. The β-Glo reagent (Promega) was used to monitor LacZ activity. The reagent was diluted 3:1 with water. Then each well was supplemented with 15 µL of the diluted β-Glo reagent using the Multiflo automated dispenser, manually shaken to mix, and incubated in the dark at room temperature for 10 min. Total end-point luminescence was then determined on a Synergy H1MF plate reader (Biotek).

The same screen was also carried out in an identical fashion in clear-bottom 384-well plates. After 12 h incubation, $OD_{600\ nm}$ (rather than luminescence) was determined, which was used to identify compounds that inhibited growth under out experimental conditions. A cell-free assay was conducted to identify compounds that interfered with the LacZ assay. A sterile culture tube carrying LB-Mops was inoculated with the phzB2-lacZ reporter strain. After overnight growth at 30° C./250, 20 mL of LB-Mops in 8×125 mL Erlenmeyer flasks were inoculated an initial $OD_{600\ nm}$ of 0.05. The cultures were grown at 30° C./250 rpm for 12 h, at which point the cells were collected by centrifugation (30 min, 4000 g), resuspended in LB-Mops, lysed by sonication, and cell debris removed by centrifugation (30 min, 4000 g). The supernatant was diluted 100-fold into LB-Mops and plated into six sterile 384 well plates as described above. Compounds from an FDA-approved drug library were added and after 5 min incubation, the b-Glo LacZ assay was carried out as described above. Compounds that inhibited the LacZ assay>1.5-fold, as compared to an untreated control, were deemed assay inhibitors.

Hit validation by LacZ assays or HPLC-MS analysis focused on compounds that downregulated virulence, while not inhibiting the growth of *P. aeruginosa* or enhanced virulence, relative to an untreated control. Assays were carried out in 50 mL Erlenmeyer flasks containing 10 mL of LB-Mops. For LacZ assays, an appropriate reporter strain from an LB agar plate was used to inoculate 5 mL of LB-Mops in a sterile 14 mL bacterial culture tube. After 4 h, $OD_{600\ nm}$ was determined, and the culture subsequently diluted to an initial $OD_{600\ nm}$ of 0.05 in a 50 mL Erlenmeyer flask. The compound of interest was added from stock concentrations generated in DMSO. A control containing only DMSO was also included. Assays were typically carried out in three biological replicates. A positive control culture, phzB2-lacZ in the absence of any compounds, was grown in parallel as well. The cultures were grown at 30° C./200 rpm. After 12 h, 65 µL was removed from each culture flask and dispensed into a sterile, white 96-well plate (Corning). Each well was supplemented with 35 µL of 3:1 diluted β-Glo reagent (Promega). The plate was incubated in the dark at room temperature for 10 minutes. End-point luminescence was determined on a Biotek H1MF plate reader. To obtain IC50 values, the averaged luminescence output (used to determine LacZ activity) was plotted against the log of the concentration of the inhibitor. The data were fit to a dose-response curve using GraphPad Prism software.

HPLC-MS analysis. Direct detection and quantification of HHQ and PQS was carried out by growing wt *P. aeruginosa* under identical conditions as described above (for growth in 50 mL Erlenmeyer flasks). After 12 h at 30° C./200 rpm, each culture was extracted with an equal volume (10 mL) of ethyl acetate. The organic layer was separated, dried completely in a speedvac concentrator, resuspended in 0.5 mL of MeOH, and analysed on an Agilent HPLC-MS consisting of a liquid autosampler, a 1260 Infinity Series HPLC system coupled to a photodiode array detector and a 6120 Series ESI mass spectrometer. Samples were resolved on a reverse phase Phenomenex Luna C18 column (3 µm, 4.6×150 mm) using a gradient of 5% MeCN in water to 100% MeCN over 30 min. Both MeCN and H2O contained 0.1% (v/v) formic acid.

Pyocyanin quantification. Pyocyanin quantification was carried by a method adapted from Essar et al.[17] Briefly, *P. aeruginosa* cultures (wt or pmrB::Tn) were prepared as described above (for growth in 50 mL Erlenmeyer flasks). The cultures contained either guanfacine (at final concentrations indicated in the figure legends) or the same volume of DMSO as control. After 12 h growth at 30° C./200 rpm, a 5 mL aliquot was removed and extracted with 3 mL dichloromethane. The organic layer was re-extracted with 1 mL 0.2 N HCl. 120 µL of this extract was transferred to a clear 96-well plate and the OD520 nm was recorded using a plate reader. The concentration of pyocyanin is proportional to OD520 nm with an extinction coefficient of 2400 M-1 cm1.

Those skilled in the art will recognize or be able to ascertain using no more than routine experimentation many equivalents to the specific embodiments of the invention described herein. Such equivalents are intended to be encompassed by the following claims.

What is claimed:

1. A method for treating a patient with an infection from *Pseudomonas aeruginosa* via virulence factor inhibition, comprising steps of:
    administering to the patient a therapeutically effective dose of guanfacine, an analog or derivative of guanfacine, or a pharmaceutically acceptable salt thereof,
    wherein the analog or derivative of guanfacine has the structure $R^1$—$R^2$—CONH—$R^3$, where $R^1$ is an optionally substituted phenyl or benzyl group, $R^2$ is a methylene unit or a C1-C6 alkyl group that is saturated or unsaturated, and $R^3$ is a carboxamidine.

2. The method according to claim 1, further comprising administering to the patient at least one antibacterial agent.

3. The method according to claim 1, wherein the therapeutically effective dose is a dose having a concentration of guanfacine, analog or derivative of guanfacine, or pharmaceutically acceptable salt thereof of less than 100 µM.

4. A method for inhibiting production of at least one virulence factor in a bacterial pathogen, comprising steps of:
    contacting the bacterial pathogen with guanfacine, an analog or derivative of guanfacine, or a pharmaceutically acceptable salt thereof,
    wherein the analog or derivative of guanfacine has the structure $R^1$—$R^2$—CONH—$R^3$, where $R^1$ is an optionally substituted phenyl or benzyl group, $R^2$ is a methylene unit or a C1-C6 alkyl group that is saturated or unsaturated, and $R^3$ is a carboxamidine.

5. The method according to claim 4, wherein the bacterial pathogen is *Pseudomonas aeruginosa*.

6. The method according to claim 4, further comprising administering to the patient at least one antibacterial agent.

7. The method according to claim 4, wherein two or more virulence factors are inhibited.

8. The method according to claim 4, wherein the at least one virulence factor is selected from the group consisting of a phenazine, alkaline protease, Pseudomonas quinolone signal (PQS), hydrogen cyanide, phospholipase C, pyocyanin, alginate, and biofilm.

9. The method according to claim 4, wherein at least seven virulence factors are inhibited.

10. The method according to claim 4, wherein the guanfacine, analog or derivative of guanfacine, or pharmaceutically acceptable salt thereof targets at least a QseC homolog in the bacterial pathogen.

* * * * *